(12) United States Patent
Rossignol-Castera et al.

(10) Patent No.: US 11,684,563 B2
(45) Date of Patent: Jun. 27, 2023

(54) PLANT DERIVED ACTIVE INGREDIENT COMPRISING PLANT EXTRACTS

(71) Applicant: DONCAB, Aix-en-Provence (FR)

(72) Inventors: Anne Rossignol-Castera, Lunel (FR); Annabelle L'Hermitte, Beaulieu (FR)

(73) Assignee: DONCAB, Aix-en-Provence (FR)

( * ) Notice: Subject to any disclaimer, the term of this patent is extended or adjusted under 35 U.S.C. 154(b) by 0 days.

(21) Appl. No.: 17/149,368

(22) Filed: Jan. 14, 2021

(65) Prior Publication Data
US 2022/0218592 A1 Jul. 14, 2022

(51) Int. Cl.
| | | |
|---|---|---|
| A61K 36/00 | (2006.01) |
| A61K 8/9789 | (2017.01) |
| A61K 36/63 | (2006.01) |
| A61K 36/185 | (2006.01) |
| A61K 36/73 | (2006.01) |
| A61K 8/92 | (2006.01) |
| A61K 8/31 | (2006.01) |
| A61K 47/14 | (2017.01) |
| A61K 47/24 | (2006.01) |
| A61K 8/37 | (2006.01) |
| A61K 8/55 | (2006.01) |
| A61Q 19/08 | (2006.01) |

(52) U.S. Cl.
CPC .............. *A61K 8/9789* (2017.08); *A61K 8/31* (2013.01); *A61K 8/375* (2013.01); *A61K 8/553* (2013.01); *A61K 8/922* (2013.01); *A61K 36/185* (2013.01); *A61K 36/63* (2013.01); *A61K 36/73* (2013.01); *A61K 47/14* (2013.01); *A61K 47/24* (2013.01); *A61Q 19/08* (2013.01); *A61K 2236/35* (2013.01); *A61K 2236/37* (2013.01)

(58) Field of Classification Search
CPC ...................................................... A61K 8/553
See application file for complete search history.

(56) References Cited

U.S. PATENT DOCUMENTS

2008/0241084 A1* 10/2008 Siddiqui ............... A61K 36/45
424/62

FOREIGN PATENT DOCUMENTS

| | | |
|---|---|---|
| FR | 2 943 684 A1 | 10/2010 |
| GB | 501732 A | 2/1939 |
| JP | 08104646 A * | 4/1996 |
| JP | H11-71291 A | 3/1999 |
| JP | 2012-206957 A | 10/2012 |
| WO | 2009/122045 A2 | 10/2009 |

OTHER PUBLICATIONS

Jabeur et al., "Contribution of Phenolic Composition to the Antioxidant, Anti-Inflammatory and Antitumor Potential of Equisetum Giganteum L. and Tilia Platyphyllos Scop." Food Function, Royal Society of Chemistry, 2007, pp. 1-32.
Kim et al., "Chemical Constituents of Tilia Taquetti Leaves and Their Inhibition of MMP-1 Expression and Elastase Activities," Natural Product Communications, 2014, vol. 9, No. 12, pp. 1683-1685.
Yamamoto et al., "Identification of Quince Varieties Using SSR Markers Developed from Pear and Apple," Breeding Science, 2004, vol. 54, pp. 239-244.

* cited by examiner

*Primary Examiner* — Quiwen Mi
(74) *Attorney, Agent, or Firm* — Oliff PLC

(57) ABSTRACT

A plant derived active ingredient and a cosmetic and a drug composition including the plant derived ingredient including: an extract from at least one plant of the gender *Olea*, an extract from at least one plant of the gender *Tilia* and/or an extract from at least one plant of the gender *Cydonia*.

13 Claims, 1 Drawing Sheet

VW=very weak; W=weak; M=moderate; FC= Fairly clear; C=clear; VC=very clear; S=strong

PLANT DERIVED ACTIVE INGREDIENT COMPRISING PLANT EXTRACTS

PRIOR ART

Plant extract are used since a long time for their benefits in cosmetics or pharmaceuticals applications.

Linden is a plant of the gender *Tilia*. *Tilia platyphyllos* is a tree frequently encountered in middle and eastern regions of France. In the ancient Gaul, linden was the traditional tree in center of the village under which the inhabitants used to gather.

Linden dried bracts are commonly consumed in herbal teas: antispasmodic, sedative, digestive, slightly diuretic, expectorant and perspirant. The dried sapwood is consumed as a decoction as a drainer of the liver and kidneys, especially in case of uric acid overload, renal or biliary lithiasis and digestive spasms. Its charcoal has been used in medicine for the treatment of digestive problems, it can also sanitize burns.

JPH1171291 discloses an aqueous extract od a plant of the gender *Tilia* as an immunoactivator.

I. Jabeur et al., Food Funct., 2017 discloses the antioxidant, anti-inflammatory and antitumor potentials of *Equisetum giganteum* L. and *Tilia platyphyllos* extracts.

Su Yeong Kim et al., Natural product communications, 2014, Vol. 9, No. 12, 16683-1685 discloses the effects of *Tilia taquetii* ethanolic extracts on inhibition of MMP-1 expression and elastase activities.

The Quince tree is a plant of the gender *Cydonia*. *Cydonia oblonga* is a tree native to Asia Minor, the Caucasus, and the Caspian region. Quince is an ancient fruit, its cultivation preceded that of the apple. Among the ancient Greeks, the quince was a ritual gift for weddings.

Quince extracts has several biological activities like antimicrobial (skin of the fruit), antioxidant (leaves and fruits), healing (seeds).

GB501732 discloses a cosmetic composition in an emulsion form comprising olive oil and quince seed extract.

JP20122206957 discloses a collagen production promoter made from an extract of a *Cydonia oblonga* seed.

The olive tree is a plant of the gender *Olea*. *Olea europa* is found in the Mediterranean region of Europe, Asia, and North Africa. Symbol of longevity and hope, it is reputed to be eternal throughout the Mediterranean region, it is also a symbol of peace, reconciliation, victory, and strength.

Olive extracts are known to have antimicrobial and antioxidant properties.

WO2009122045 discloses the use of olive oil extract to control skin aging.

DETAILED DESCRIPTION OF THE INVENTION

Figure 1:
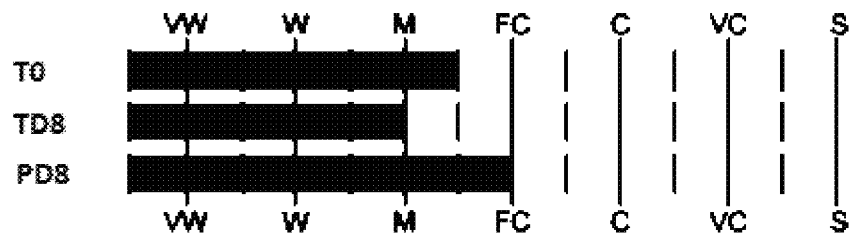
FIG. 1 illustrates the staining strength of collagen I in the papillary dermis of all the batches of human skin explants.

The present invention is about a plant derived active ingredient comprising:

An extract from at least one plant of the gender *Olea*,

An extract from at least one plant of the gender *Tilia* and/or an extract from at least one plant of the gender *Cydonia*.

In an embodiment, the at least one plant of the gender *Olea* is selected from the group consisting of *Olea europaea*, *Olea paniculata*, *Olea ambrensis*, *Olea capensis*, *Olea undulata*, *Olea woodiana*, *Olea lancea*, *Olea caudatilimba*, *Olea brachiata*, *Olea guangxiensis*, *Olea hainanensis*, *Olea laxiflora*, *Olea neriifolia*, *Olea parvilimba*, *Olea rosea*, *Olea salicifolia*, *Olea tetragonoclada*, *Olea tsoongii*, *Olea chrysophylla*, *Olea exasperata*, *Olea hochstetteri*, *Olea welwitschii*, alone or in combination.

In a preferred embodiment, the at least one plant of the gender *Olea* is *Olea europaea*.

In an embodiment, the at least one plant of the gender *Tilia* is selected from the group consisting of *Tilia platyphyllos*, *Tilia americana*, *Tilia heterophylla*, *Tilia miqueliana*, *Tilia amurensis*, *Tilia mongolica*, *Tilia begoniifolia*, *Tilia monticola*, *Tilia caroliniana*, *Tilia nasczokinii*, *Tilia neglecta*, *Tilia chenmoui*, *Tilia nobilis*, *Tilia occidentalis*, *Tilia chinensis*, *Tilia chingiana*, *Tilia cordata*, *Tilia orbicularis*, *Tilia oliveri*, *Tilia croizatii*, *Tilia paucicostata*, *Tilia petiolaris*, *Tilia dasystyla*, *Tilia endochrysea*, *Tilia floridana*, *Tilia henryana*, *Tilia heterophylla*, *Tilia hilliéri*, *Tilia hupehensis*, *Tilia insularis*, *Tilia intonsa*, *Tilia japonica*, *Tilia kiusiana*, *Tilia koreana*, *Tilia ledebourii*, *Tilia mandshurica*, *Tilia maximowicziana*, *Tilia mexicana*, *Tilia rubra*, *Tilia sibirica*, *Tilia taquetii*, *Tilia tuan*, *Tilia tomentosa*, *Tilia varsaviensis*, *Tilia zaeskania*, alone or in combination.

In a preferred embodiment, the at least one plant of the gender *Tilia* is *Tilia platyphyllos*.

In an embodiment, the at least one plant of the gender *Cydonia* is *Cydonia oblonga*.

*Cydonia oblonga* is also known as *Cydonia vulgaris* or *Pyrus Cydonia*. The *Cydonia oblonga* plant used herein can be of various varieties alone or in combination, for example it can be one of the varieties listed and identified in the publication: Yamamoto et al.; Breeding Science; 54:239-244 (2004)

In an embodiment, the plant extracts originate from leaves, fruits, flowers, roots, seeds, stems, bark, or wood of said plants.

In a preferred embodiment, the extract from at least one plant of the gender *Olea* originates from the fruits of said plant.

In a preferred embodiment, the extract from at least one plant of the gender *Tilia* originates from the flowers of said plant.

In an embodiment, the extract from at least one plant of the gender *Cydonia* originates from the leaves of said plant.

In an embodiment, the plant extracts are in a plant-part form, a powder form, an aqueous form, or an oily form.

By "plant-part form", it means that the extract is constituted of fragments or complete parts of a plant.

In a preferred embodiment, the extract from at least one plant of the gender *Olea* is in an oily form.

An extract of *Olea europaea* can comprise numerous phenolic compounds as for example phenolic alcohols (tyrosol, hydroxytyrosol, verbascoide), phenolic acids (caffeic acid, vanillic acid), flavonoids (apigenin, luteolin, rutin), secoiridoids (oleuropein, ligstroside), lignanes (cycloolivil).

In an embodiment, the extract from at least one plant of the gender *Olea* comprises from 0.001 to 1% by weight of polyphenols in relation to the total weight of the extract.

In an embodiment, the extract from at least one plant of the gender *Olea* comprises from 0.005 to 0.5% by weight of polyphenols in relation to the total weight of the extract.

In an embodiment, the extract from at least one plant of the gender *Olea* comprises from 0.01 to 0.1% by weight of polyphenols in relation to the total weight of the extract.

In an embodiment, the extract from at least one plant of the gender *Olea* comprises a polyphenols concentration from 50 to 5000 mg/kg.

In an embodiment, the extract from at least one plant of the gender *Olea* comprises a polyphenols concentration from 100 to 3000 mg/kg.

In an embodiment, the extract from at least one plant of the gender *Olea* comprises a polyphenols concentration from 500 to 1000 mg/kg.

The concentration in polyphenols is calculated in mg/kg oleuropein equivalent in this application.

In a preferred embodiment, the extract from at least one plant of the gender *Tilia* is in a powder form.

An extract of *Tilia platyphyllos* can comprise at least 33 different polyphenolic compounds: 3 phenolic acids and 30 flavonoids mainly quercetin and kaempferol derivatives. It further comprises carotenoids as for example lutein and β-carotene.

In an embodiment, the extract from at least one plant of the gender *Tilia* comprises from 1 to 30% by weight of polyphenols in relation to the total weight of the extract.

In an embodiment, the extract from at least one plant of the gender *Tilia* comprises from 5 to 25% by weight of polyphenols in relation to the total weight of the extract.

In an embodiment, the extract from at least one plant of the gender *Tilia* comprises from 10 to 20% by weight of polyphenols in relation to the total weight of the extract.

In an embodiment, the extract from at least one plant of the gender *Tilia* comprises a polyphenols concentration from 10,000 to 500,000 mg/kg.

In an embodiment, the extract from at least one plant of the gender *Tilia* comprises a polyphenols concentration from 50,000 to 300,000 mg/kg.

In an embodiment, the extract from at least one plant of the gender *Tilia* comprises a polyphenols concentration from 100,000 to 200,000 mg/kg.

In a preferred embodiment, the extract from at least one plant of the gender *Cydonia* is in a powder form.

An extract of *Cydonia oblonga* can comprise numerous phenolic compounds as for example flavonoids, glycosylated flavonoids, chlorogenic acids. It further comprises organic acids, sugars, amino acids, fatty acid esters, triterpene compounds, carotenoids.

In an embodiment, the extract from at least one plant of the gender *Cydonia* comprises from 10 to 60% by weight of polyphenols in relation to the total weight of the extract.

In an embodiment, the extract from at least one plant of the gender *Cydonia* comprises from 20 to 50% by weight of polyphenols in relation to the total weight of the extract.

In an embodiment, the extract from at least one plant of the gender *Cydonia* comprises from 30 to 40% by weight of polyphenols in relation to the total weight of the extract.

In an embodiment, the extract from at least one plant of the gender *Cydonia* comprises a polyphenols concentration from 100,000 to 600,000 mg/kg.

In an embodiment, the extract from at least one plant of the gender *Cydonia* comprises a polyphenols concentration from 200,000 to 500,000 mg/kg.

In an embodiment, the extract from at least one plant of the gender *Cydonia* comprises a polyphenols concentration from 300,000 to 400,000 mg/kg.

In an embodiment, the plant derived active ingredient according to the invention further comprises at least one surfactant.

In an embodiment, the at least one surfactant is a water in oil surfactant.

This surfactant is preferentially a "polyglyceryl" type fatty acid ester.

In an embodiment, the at least one water in oil surfactant is selected from the group consisting of polyglyceryl-4 oleate, polyglyceryl-3 diisostearate, polyglyceryl-6 dioleate, polyglyceryl-3 caprate, glycerol stearate, or phospholipids (for example lecithins), alone or in combination.

In an embodiment, the mass ratio between the extract from at least one plant of the gender *Tilia* and/or the extract from at least one plant of the gender *Cydonia* and the extract from at least one plant of the gender *Olea* is from 1:2 to 1:10 and preferably from 1:3 to 1:5.

When used together, the mass ratio between the extract from at least one plant of the gender *Cydonia* and the extract from at least one plant of the gender *Tilia* is from 1:2 to 1:10, preferably from 1:3 to 1:5, and most preferably equal to 1:4.

In an embodiment, the plant derived active ingredient according to the invention comprises a polyphenols concentration from 200 to 20,000 mg/kg.

In an embodiment, the plant derived active ingredient according to the invention comprises a polyphenols concentration from 3,000 to 16,000 mg/kg.

In an embodiment, the plant derived active ingredient according to the invention comprises a polyphenols concentration from 8,000 to 12,000 mg/kg.

In a preferred embodiment, the plant derived active ingredient according to the invention is in an oily form.

In another embodiment, the plant derived active ingredient according to the invention is in an emulsion form.

A plant extract can be obtained from different solvents.

Organic solvents such as hexane or acetone present either a health risk or an environmental risk. Ethanol is considered a skin irritant. Water is a green solvent but requires the addition of chemical preservatives to ensure microbiological stability. These disadvantages are not encountered with the use of vegetable oil as an extraction solvent.

The plant derived active ingredient according to the invention is preferably manufactured by the method disclosed in the patent FR2943684.

Vegetable oils are in fact green solvents, derived from renewable agricultural sources and have no impact on the environment and health. Vegetable oils are neither irritating nor allergenic on the skin. They do not require any chemical preservatives or other additives because they do not present any microbiological risk. They naturally contain active compounds in the skin such as polyunsaturated fatty acids omega 3 or omega 6 or vitamin E.

In addition, oily extracts can be directly and easily formulated in an emulsion but also in an anhydrous cosmetic product, i.e. without an aqueous phase, or with a continuous fatty phase, such as an anti-ageing oily serum, a repairing care oil or a make-up.

Oily plant extracts therefore have many advantages over other forms of extracts.

In a preferred embodiment, the plant derived active ingredient according to the invention is obtainable by means of an extraction method comprising the following steps:

a) mixing and impregnating the extract from at least one plant of the gender *Tilia* and/or the extract from at least one plant of the gender *Cydonia* in a powder form with the extract from at least one plant of the gender *Olea* in an oily form at a temperature which is greater than the melting point of said extract from at least one plant of the gender *Olea* and under an atmosphere which is depleted or essentially depleted in oxygen, b) heating to a temperature between 80 to 200° C. during less than 10 minutes by means of microwaves and under an atmosphere which is depleted or essentially depleted in oxygen, c) microdispersing said extract from at least one plant of the gender *Tilia* and/or said extract from at least one plant of the gender *Cydonia* into said extract from at least one plant of the gender *Olea* at a temperature which is greater than the melting point of said extract from at least one plant of the gender *Olea* and under an atmosphere which is depleted or essentially depleted in oxygen, by means of ultrasonic cavitation treatment, step c) being able to be implemented before, during or after step b).

In an embodiment, at step a) is added at least one surfactant acting as co-extractant, preferably a water in oil surfactant.

This surfactant is preferentially a "polyglyceryl" type fatty acid ester.

In an embodiment, the at least one water in oil surfactant is selected from the group consisting of polyglyceryl-4 oleate, polyglyceryl-3 diisostearate, polyglyceryl-6 dioleate, polyglyceryl-3 caprate, glycerol stearate, or phospholipids (for example lecithins), alone or in combination.

In an embodiment, said treatment by ultrasonic cavitation of step c) is carried out for a period between 2 and 30 minutes, at a cavitation frequency of less than 100 kHz.

In an embodiment, step a) and b) and c) are carried out under nitrogen atmosphere.

The present invention further concerns a cosmetic composition comprising the plant derived active ingredient according to the invention.

In an embodiment, the cosmetic composition according to the invention comprises from 0.1 to 10% by weight of said plant derived active ingredient in relation to the total weight of the composition.

In a preferred embodiment, the cosmetic composition according to the invention comprises from 1 to 5% by weight of said plant derived active ingredient in relation to the total weight of the composition.

In a particularly preferred embodiment, the cosmetic composition according to the invention comprises from 2 to 4% by weight of said plant derived active ingredient in relation to the total weight of the composition.

In an embodiment, the cosmetic composition according to the invention is in the form of a cream, a shampoo, a gel, an emulsion, a milk, a lotion, a serum, an ointment, a foam, an essence, an oil, a wax, a stick, a powder, encapsulated, an injectable solution, and more generally in all cosmetic products as defined in the EC Directive 1223/2009 relating to cosmetic products.

In an embodiment, the cosmetic composition according to the invention further comprises at least one excipient chosen from the group consisting of solvents, denaturants, humectants, perfumes, viscosity control agents, emulsifiers, surfactants, emollients, foam boosters, hair care agents, hydrotropes, skin care agents, fixing agents, emulsion stabilizers, gelling agents, antioxidants, preservatives, chelating agents, pH regulators, masking agents, film-forming agents, adsorbents, hair fixatives, oral hygiene agents, deodorants, cosmetic dyes, opacifiers, lipid restoratives, UV filters, UV absorbers, abrasive agents, anti-caking agents, fillers, cleaning agents, antifoaming agents, moisturizing agents, foaming agents, antistatic agents, plasticizing agents, antimicrobial agents, softening agents, emollients, toning agents, emulsion stabilizers, and binders, alone or in combination.

The present invention further concerns a drug composition comprising the plant derived active ingredient according to the invention.

In an embodiment, the drug composition according to the invention is in a pharmaceutical form selected from the group consisting of an oral form, injectable form, dermal form, rectal form, inhaled form.

In an embodiment, the drug composition according to the invention is in an oral form.

In an embodiment, the oral form is selected in the group consisting of a tablet, an effervescent tablet, a dispersable tablet, a sublingual tablet, a capsule, a syrup, an oral solution, a drinkable suspension.

In an embodiment, the drug composition according to the invention is in an injectable form.

In an embodiment, the drug composition according to the invention is in a dermal form.

In an embodiment, the dermal form is selected in the group consisting of an ointment, a lotion, a gel, a solution, patch.

In an embodiment, the drug composition according to the invention is in a rectal form.

In an embodiment, the drug composition according to the invention is in an inhaled form.

The present invention further concerns the use of the plant derived active ingredient according to the invention for the manufacture of a cosmetic composition.

The present invention further concerns the use of the plant derived active ingredient according to the invention for the manufacture of a drug composition.

The present invention further concerns the use of the plant derived active ingredient according to the invention for increase of collagen synthesis in a subject.

In an embodiment, collagen is type I collagen.

EXAMPLES

Example 1: Manufacture of a Plant Derived Active Ingredient According to the Invention 80 g of flowering tops of *Tilia platyphyllos* plant and 20 g of leaves of *Cydonia oblonga* plant, are air-dried and then crushed at −80° C. with a knife mill for 1 min to obtain a fine, homogeneous powder. The average final particle size is between about 200 and 300 microns. The resulting powder is then mixed with 500 ml of *Olea europaea* oil.

Oily impregnation is carried out in a closed system for 2 hours after nitrogen bubbling and at room temperature.

The oily impregnation is followed by an intensified extraction carried out under nitrogen sweeping and the mixture is submitted to 800 watts of microwave power in 2×3 min. The maximum temperature reached is 145° C.

The last step is a micro-dispersion of plant powder conducted always under nitrogen sweeping and under an ultrasonic frequency of 20 kHz for 2×3 min.

Then the oil is separated by centrifugation at 5000 rpm for 5 min and then filtered.

The content of total phenolic compounds measured by the Ciocalteau FoNn method in oleuropein equivalent is 475 mg/kg for the oily extract obtained by the process.

Example 2: Manufacture of a Plant Derived Active Ingredient According to the Invention with Addition of Polyglyceryl-4 Oleate The process is equivalent as in the example 1 except that the plant powder is mixed with *Olea europaea* oil plus polyglyceryl-4 oleate acting as co-extractant.

The content of total phenolic compounds measured by the Ciocalteau FoNn method in oleuropein equivalent is 10,743 mg/kg, it represents a gain in polyphenols of +2162%, i.e. a concentration of phenols multiplied more than 22 times.

Example 3: Cosmetic Composition Comprising a Plant Derived Active Ingredient According to the Invention

TABLE 1

Facial oil composition comprising a plant derived active ingredient according to the invention

| Ingredient (INCI name) | Percentage |
|---|---|
| SQUALANE | 34% |
| SIMMONDSIA CHINENSIS SEED OIL | 29% |
| CAMELINA SATIVA SEED OIL | 19.5% |
| PRUNUS ARMENIACA KERNEL OIL | 14.5% |
| Plant derived active ingredient according to the invention | 3% |

Example 4: Assessment of the Activity of a Plant Derived Active Ingredient According to the Invention on the Stimulation of Collagen I Synthesis on Human Living Skin Explants Ex Vivo Aim of the Study:

Evaluate a boost in the collagen I synthesis of a plant derived active ingredient according to the invention on human living skin explants ex vivo. The activity has been evaluated by a control of the cell viability after Masson's trichrome staining and an immunostaining of collagen I.

Material & Methods:

The study is scheduled on 8 days.

9 human skin explants of an average diameter of 12 mm (+/−1 mm) were prepared on an abdoplasty coming from a 65-year-old Caucasian woman with a phototype II. The explants were kept in survival in BEM culture medium (BIO-EC's Explants Medium) at 37° C. in a humid, 5% $CO_2$ atmosphere.

The plant derived active ingredient according to the invention (A) was diluted at 1% paraffin oil (product P) for the batch P. The diluted solution P was stored at 4° C., in the dark, during the study and well homogenized before each treatment. The explants were distributed into 3 batches.

TABLE 2

Distribution of the 9 human skin explants

| Batches | Designation | Treatment | Number of explants | Sampling time |
|---|---|---|---|---|
| T0 | Control of the tissue | / | 3 | Day 0 |
| T | Blank batch | / | 3 | Day 8 |
| P | Product P | A at 1% | 3 | Day 8 |

The tested product P was applied topically based on 2 μl per explant (2 mg/cm$^2$) and spread using a small spatula on day 0 (D0), D1, D4, D5, D6 and D7. The control explants T did not receive any treatment except the renewal of culture medium. The culture medium was half renewed (1 ml per well) on D1, D4 and D6.

On D0, the 3 explants from the batch T0 were collected and cut in two parts. Half was fixed in buffered formalin solution and half was frozen at −80° C. On D8, 3 explants from all batches were collected and treated in the same way than in D0.

After fixation for 24 hours in buffered formalin, the samples were dehydrated and impregnated in paraffin using a Leica PEARL dehydration automat. The samples were embedded using a Leica EG 1160 embedding station. 5-μm-thick sections were made using a Leica RM 2125 Minot-type microtome, and the sections were mounted on Super-frose® histological glass slides. The frozen samples were cut into 7-pm-thick sections using a Leica CM 3050 cryostat. Sections were then mounted on Superfrost® plus silanized glass slides. The microscopical observations were realized using a Leica DMLB and an Olympus BX43 or BX63 microscope. Pictures were digitized with a numeric DP72 or DP74 Olympus camera with cellSens (Olympus) storing software.

The cell viability of the epidermal and dermal structures was assessed by microscopical observation of formalin-fixed paraffin embedded skin sections after Masson's trichrome staining, Goldner variant.

Collagen I immunostaining was performed on frozen sections with a polyclonal anti-collagen I antibody (Monosan, ref. PS047) diluted at 1:100 in PBS-BSA 0.3%-Tween 20 at 0.05% and incubated for 1 hour at room temperature and revealed by AlexaFluor488 (Lifetechnologies, ref. A11008). The nuclei were counterstained with propidium iodide. The immunostaining was performed using an automated slide processing system (Autostainer, Dako) and assessed by microscopical observation.

Results:

TABLE 3

Results of cell viability

| | Cell viability | |
|---|---|---|
| Batch | Epidermis | Dermis |
| T0 | Good | Good |
| TD8 | Fairly Good | Good |
| PD8 | Fairly Good | Good |

On D0, on the blank batch T0, the cell viability is good in the epidermis and in the dermis. On D8, on the blank batch TD8, the cell viability is good in the epidermis and good in the dermis. The product P induces no modification.

The staining of collagen I in the papillary dermis of all the batches is shown in FIG. 1.

On day 0, on the blank batch T0, the staining of collagen I is moderate to clear in the papillary dermis. On day 8, on the blank batch TD8, collagen I expression is moderate in the papillary dermis. The product P induces a moderate increase.

Conclusion:

The product P stimulates the expression of collagen I on human living skin explants ex vivo after 8 days of treatment, so the plant derived active ingredient according to the invention induces a boost in collagen I synthesis.

Example 4: Image Analysis of Collagen I Immunostaining Performed in Example 1

Image Analysis Method:

The images analyses were performed on all the images of each batch, according to method using Cell^D software. The stained surface percentage (Surf %) for each treatment is compared to the untreated condition: P vs T.

Results:

TABLE 4

Percentage of surface positive to collagen I immunostaining in the papillary dermis for the concerned batches

| Image | Collagen I in the papillary surface (% surface) | |
| --- | --- | --- |
| | TD8 | PD8 |
| 1 | 42.7 | 53.5 |
| 2 | 42.8 | 79.4 |
| 3 | 61.1 | 59.7 |
| 4 | 69.1 | 74.6 |
| 5 | 64.4 | 86.1 |
| 6 | 44.0 | 87.3 |
| 7 | 45.6 | 74.6 |
| 8 | 47.9 | 64.7 |
| 9 | 61.9 | 65.1 |
| Mean | 53.3 | 71.7 |
| Standard deviation | 10.6 | 11.7 |

Figure 2:
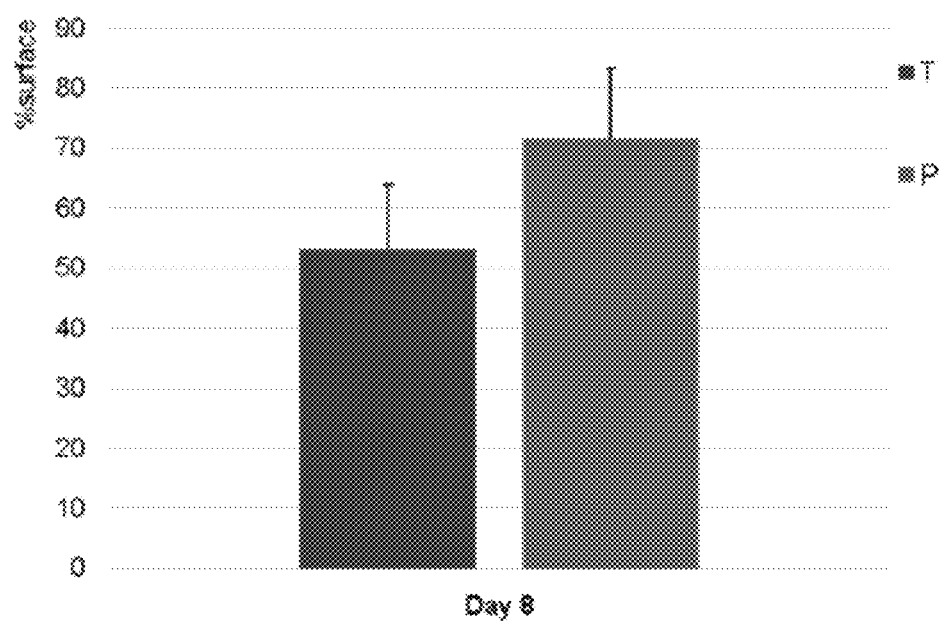
FIG. 2 illustrates the surface percentage positive to collagen I in the papillary dermis on day 8 for the blank batch T and the product P.

On day 8, On the blank batch TDB, the staining of collagen I represents 53.3% of the surface of the papillary dermis. The product P induces a significant increase of 35% illustrated in FIG. 2.

CONCLUSIONS

The product P significantly stimulates the expression of collagen I on human living skin explants ex vivo after 8 days of treatment, so the plant derived active ingredient according to the invention induces a boost in collagen I synthesis.

The invention claimed is:

1. A plant derived active ingredient comprising:
an extract from at least one plant of the gender *Olea*, and
an extract from at least one plant of the gender *Tilia* and/or an extract from at least one plant of the gender *Cydonia*,
wherein the mass ratio between the extract from at least one plant of the gender *Tilia* and/or the extract from at least one plant of the gender *Cydonia* and the extract from at least one plant of the gender *Olea* is from 1:2 to 1:10, and
wherein the plant derived active ingredient is obtained by an extraction method comprising:
a) mixing and impregnating the extract from at least one plant of the gender *Tilia* and/or the extract from at least one plant of the gender *Cydonia* in a powder form with the extract from at least one plant of the gender *Olea* in an oily form and polyglyceryl-4-oleate at a temperature greater than a melting point of the extract from at least one plant of the gender *Olea* and under an atmosphere which is depleted or essentially depleted in oxygen to obtain an oily impregnation,
b) heating the oily impregnation to a temperature between 80 to 200° C. for less than 10 minutes by means of microwaves and under an atmosphere which is depleted or essentially depleted in oxygen, and
c) forming a microdispersion from the heated oily impregnation at a temperature greater than the melting point of the extract from at least one plant of the gender *Olea* and under an atmosphere which is depleted or essentially depleted in oxygen, by means of ultrasonic cavitation treatment,
step c) being conducted before, during or after step b), and
d) separating oil from the microdispersion to obtain the plant derived active ingredient.

2. The plant derived active ingredient according to claim 1 wherein the at least one plant of the gender *Olea* is *Olea europaea*.

3. The plant derived active ingredient according to claim 1 wherein the at least one plant of the gender *Tilia* is *Tilia platyphyllos*.

4. The plant derived active ingredient according to claim 1 wherein the at least one plant of the gender *Cydonia* is *Cydonia oblonga*.

5. The plant derived active ingredient according to claim 1 wherein in addition to polyglyceryl-4-oleate, the plant derived active ingredient further comprises at least one additional surfactant.

6. The plant derived active ingredient according to claim 5 wherein the at least one additional surfactant comprises a water in oil surfactant selected from the group consisting of polyglyceryl-3 diisostearate, polyglyceryl-6 dioleate, polyglyceryl-3 caprate, glycerol stearate, phospholipids, and combinations thereof.

7. The plant derived active ingredient according to claim 1 wherein the plant derived active ingredient comprises a polyphenols concentration from 200 to 20,000 mg/kg.

8. A cosmetic composition comprising the plant derived active ingredient according to claim 1.

9. A drug composition comprising the plant derived active ingredient according to claim 1.

10. The plant derived active ingredient according to claim 1 wherein the plant derived active ingredient has a polyphenols concentration of from 3,000 to 20,000 mg/kg provided from the extract from at least one plant of the gender *Tilia* and/or the extract from at least one plant of the gender *Cydonia* and the extract from at least one plant of the gender *Olea*.

11. The plant derived active ingredient according to claim 1 wherein the extraction method further includes a step e) of filtering the oil obtained in step d).

12. A method for increasing collagen synthesis in a subject comprising administering to the subject the plant derived active ingredient according to claim 1.

13. The method according to claim 12, wherein collagen is type I collagen.

* * * * *